United States Patent [19]

Coleman

[11] 3,985,124

[45] Oct. 12, 1976

[54] SPIROMETER

[75] Inventor: Steven J. Coleman, Marlboro, Mass.

[73] Assignee: Thermo Electron Corporation, Waltham, Mass.

[22] Filed: Mar. 26, 1975

[21] Appl. No.: 562,302

[52] U.S. Cl. .................................. 128/2.08; 346/72
[51] Int. Cl.² ......................................... A61B 5/08
[58] Field of Search .................. 128/2.08, 2.07, 2 C, 128/DIG. 29; 346/33 ME, 72; 73/239, 262

[56] References Cited
UNITED STATES PATENTS

| | | | |
|---|---|---|---|
| 3,086,515 | 4/1963 | Jones | 128/2.08 |
| 3,311,109 | 3/1967 | Gruen et al. | 128/2.08 |
| 3,363,260 | 1/1968 | Garbe | 128/2.08 |
| 3,722,506 | 3/1973 | McMillan, Jr. | 128/2.08 |
| 3,817,238 | 6/1974 | Matson | 128/2.08 |
| 3,848,583 | 11/1974 | Parr | 128/2.08 |
| 3,889,672 | 6/1975 | Woldring | 128/2.08 |

FOREIGN PATENTS OR APPLICATIONS 1,569,193  5/1969  France .............................. 128/2.08

Primary Examiner—Robert W. Michell
Assistant Examiner—Lee S. Cohen
Attorney, Agent, or Firm—James L. Neal

[57] ABSTRACT

A spirometer for measurement of both the rate and volume of expiratory breathing, and creating a graphic record of the same. In a preferred embodiment, the spirometer incorporates an expansible chamber of the piston type, fitted with a molded rolling rubber seal. A recording surface in the form of a card is attached to the piston and a pen is moved across the face of the card at a constant velocity as a subject breathes into the expansible chamber. There is obtained a plot of the volume of expiration flow as a function of time. A control system provides for automatic operation.

20 Claims, 5 Drawing Figures

SPIROMETER

BRIEF SUMMARY OF THE INVENTION

This invention relates to a recording spirometer of a simple design involving a recording surface mounted upon an expansible chamber for movement as a function of the expiratory flow of a patient. The recording surface is engageable by a movable stylus to provide a plot thereon.

In a preferred embodiment, the spirometer incorporates an expansible chamber of the piston type, fitted with a molded rolling rubber seal. A recording surface in the form of a card is attached to the piston and a pen is moved across the face of the card at a constant velocity as a subject breathes into the expansible chamber. There is obtained a plot of the volume of expiration flow as a function of time. A control system provides for automatic operation.

DETAILED DESCRIPTION OF THE DRAWINGS

Figure 1:
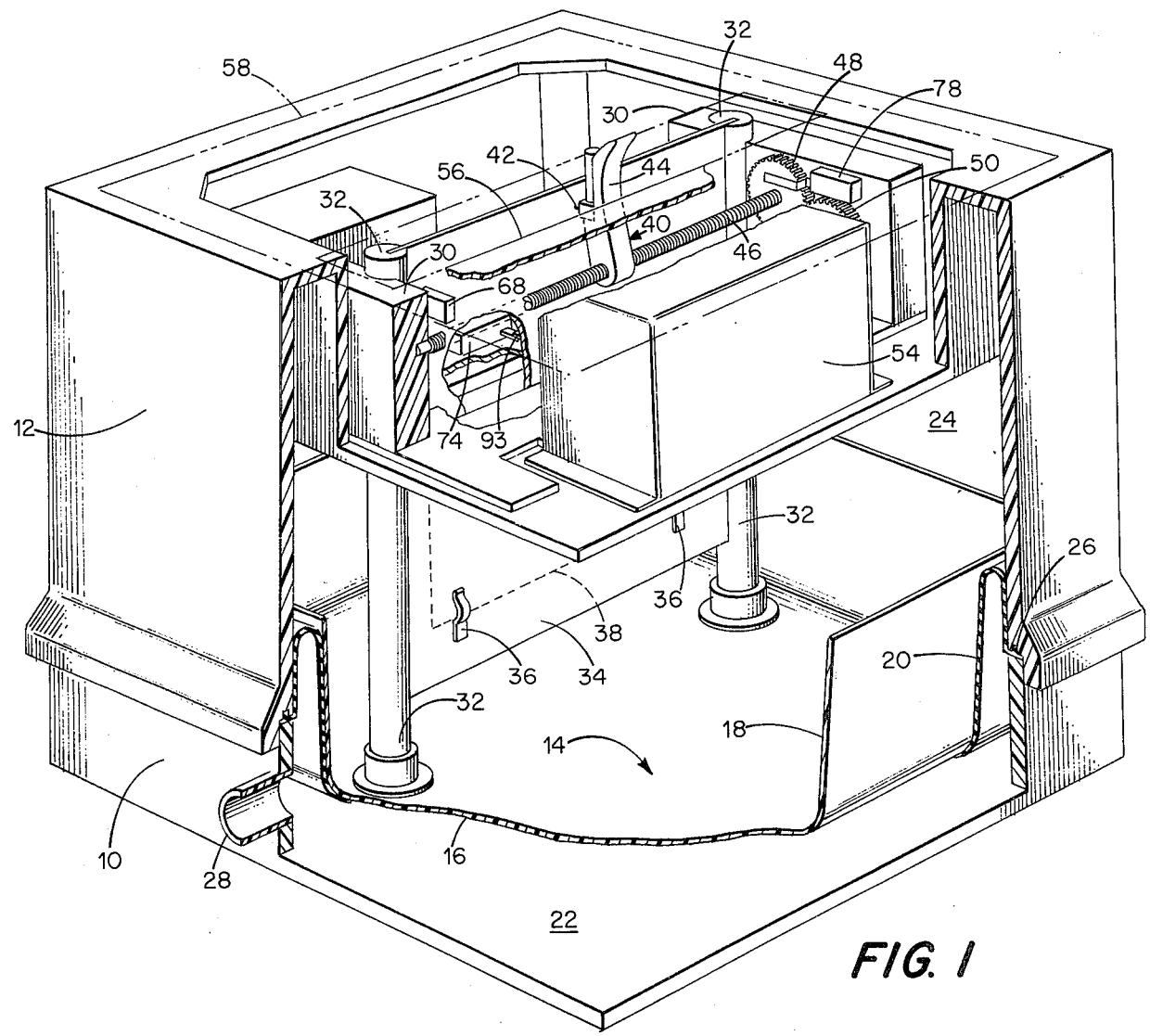
FIG. 1 is a cutaway isometric view of a preferred embodiment of the invention.

The spirometer of FIG. 1 is divided into two major sections, a lower casing 10 and an upper casing 12. A piston 14, preferably a single piece molding, forming a flat rectangular plate 16 having upturned sides 18, is located within the casings. The piston 14 and the casings 10 and 12 have substantially similar rectangular cross sectional configurations. A flexible rolling seal 20 surrounds the piston 14 and separates the inside of the device into a lower expansible chamber 22 and an upper chamber 24 which is open to the atmosphere. The rolling seal 20 may be made of a single piece of molded silicone rubber. The rolling seal 20 is clamped at its edges between the upper and lower casings 10 and 12 to provide for ease of assembling and ease of disassembling for cleaning and maintenance, and to seal lower chamber from the atmosphere. A lip 26 around the edge of the seal aids this sealing function.

Exhaled from a subject, air enters the device through an opening 28. Attached to the opening is a conduit preferably made of flexible tubing (not shown) to allow the subject to take a comfortable position during the test. The opening 28 introduces air into the expansible lower chamber 22 and displaces the piston 14 in a vertical direction.

The piston is constrained to move in a straight vertical line by the interaction of two guides 30 and mating posts 32 mounted on opposed sides of the piston 14. These guides are mounted on opposing surfaces of the upper casing 12, constructed of a lubricating thermoplastic, such as RULON, a reinforced polytetrafluoroethylene, made by Dixon Corporation. Attached between the posts is a thin plate of metal 34 fitted with clips 36 for holding paper card 38 (shown in phantom) to the plate. The two guide posts 32 are positioned so that the center of pressure of the piston is directly and equaldistantly between them, the center of pressure being the point by which the piston could be supported against air pressure with no tendency to cock. Any such tendency to cock would cause increased friction. The center of pressure for a rectangular piston is merely the geometric center, and so in the preferred embodiment the two guide posts are mounted near the center of two opposing edges.

As the piston rises in response to air forced into the expansible chamber the card moves past a marking station. In the marking station is a means 40 for applying a mark to the card as it rises. The marking means 40 includes a pen 42 mounted in a movable carriage forming a pen holder 44. The pen holder 44 is mounted on a threaded rotatable shaft 46 supported in bearing surfaces which may be conveniently formed within the same thermoplastic material forming the guides 30. A gear wheel 48 mounted on the shaft 46 mates with a gear wheel 50 driven by a motor 52 (not shown in FIG. 1) in the housing 54. The motor is thus drivably connected to the shaft for rotating it to thereby cause the pen holder 44 to traverse the shaft. The pen 42 arranged to contact the card mounted on the plate when the threaded rod 46 is rotated in a first direction. There is sufficient friction between the pen holder and the threshold shaft to force the pen against the card and to cause the pen to mark the card. When the pivotal motion of the pen holder about the threaded shaft is restrained by the pen's contact with the card 38, backed by the card holder 34, the action of the rotating threaded shaft 46 causes the pen holder 44 and pen 42 to traverse the length of the shaft from right to left as shown in FIG. 1. When the direction of rotation of the threaded shaft is reversed, the pen holder 44 rotates a fraction of a turn away from the card and engages a stop 56 and traverses back to its starting position. The stop of the preferred embodiment is conveniently formed as part of the spirometer cover 58, (shown in phantom).

The motor 52 is reversible. The preferred embodiment uses a three phase synchronous motor, which provides for a constant speed traverse of the pen holder, but a motor with a variable speed and automatic means to vary that speed in a predictable manner during the traverse could be used.

Figure 2:
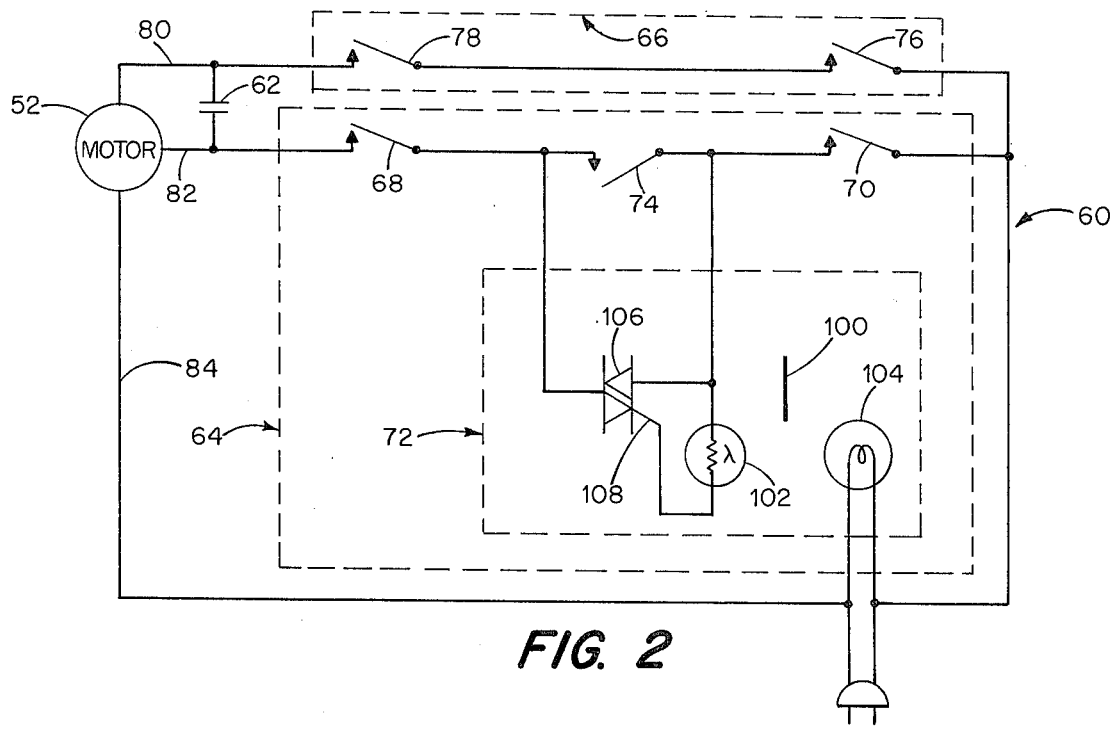
FIG. 2 is a schematic of an electrical control system usable with the embodiment of FIG. 1.

The action of the motor 52 is controlled by the electrical system 60, shown schematically in FIG. 2. The electrical system includes: a three phase (ac) motor 52, a phase shifting capacitor 62, a mark mode circuit 64 and a return mode circuit 66. The mark mode circuit 64 includes: a series circuit of a normally closed limiting switch 68; a mark mode enabling switch 70; and a parallel combination of an air flow sensitive activate switch 72 and an activate micro-switch 74. The return mode circuit 66 includes: a series circuit of a return activate switch 76 and a normally closed limiting switch 78. The electrical system further includes the following (not shown): a master on-off power switch, a pilot light, and fuse means.

The three phase motor 52 is connected as a bi-directional two phase motor as follows. A capacitor 62 is connected between leads 80 and 82 of the motor. The capacitor introduces a phase shift in one winding of the motor, thus producing three phases. The means of connection described above provides two capacitor-connected leads 80 and 82 and a common lead 84. If power is applied between one capacitor-connected lead and the common lead, the motor will rotate clockwise, if power is applied between the other capacitor-connected lead and common, the motor rotates counter-clockwise. The mark mode circuit 64, is connected to one capacitor-connected lead 82, and the return mode 66 circuit to the other capacitor-connected lead 80. When power is applied to the motor 52 through the mark mode circuit 64, the motor rotates counter-clockwise, and when power is applied through the return mode circuit 66, the motor rotates clockwise.

The system operates in the following manner. The testing physician closes the mark mode enabling switch 70. When the subject exhales one or both of the two activate switches 72 and 74 will be closed. Since these two switches 72 and 74 are wired in parallel, after either is closed current will flow through the normally closed limiting switch 68 to the motor 52 and cause it to rotate. This causes the pen 42 to be pressed against the card 38 and the pen 42 and holder 44 to traverse along the threaded shaft 46. When the pen holder 44 engages the limit switch 68, it opens the current to the motor 52 is interrupted. Rotation of the threaded shaft 46 stops.

Figure 4:
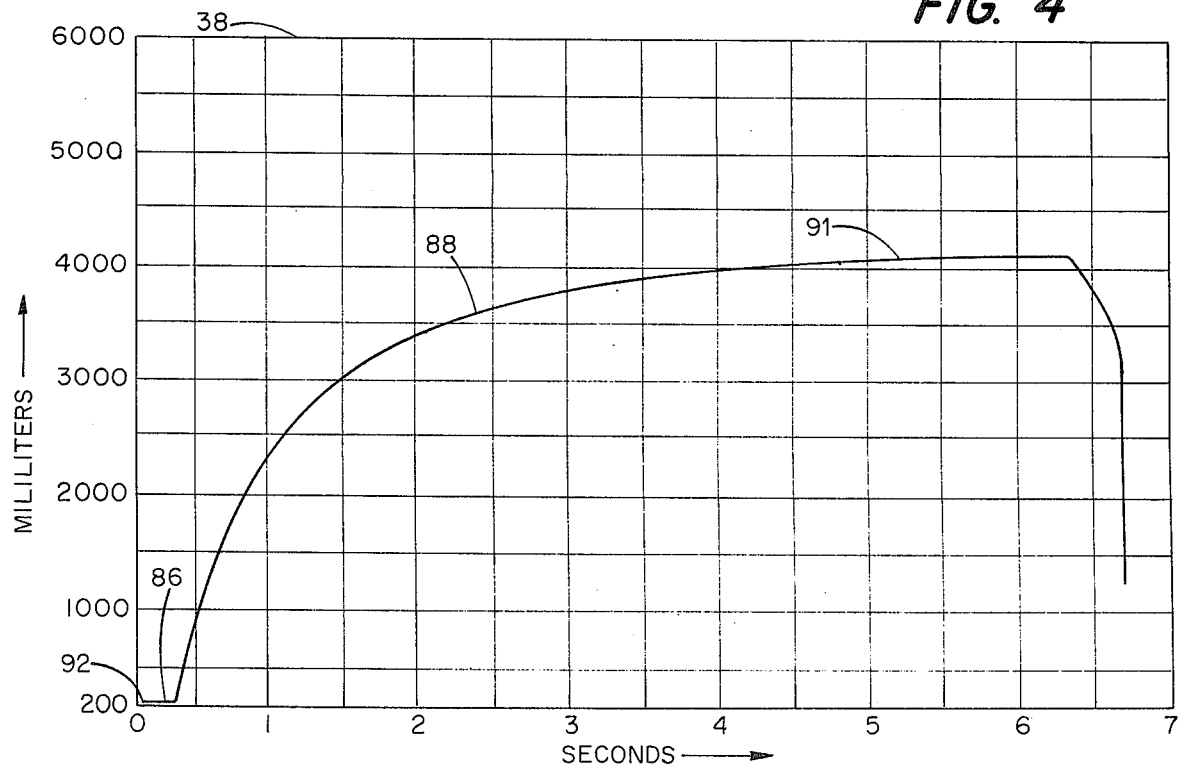
FIG. 4 depicts a record made on a paper card by the embodiment of FIG. 1.

It is desirable to use two separate switch means to activate the motor in the mark mode, one responding to motion of the piston, and the other responding to displaced air for the following reasons. A first portion of exhaled air (for example, the first 200 ml.) may enter the lower chamber 22 before the piston moves in response to such exhalation. This occurs because the rolling seal 20 inflates and shifts slightly during the initial part of exhalation. This inflation of the rolling seal displaces air in the upper chamber 24. Therefore an air activated switch 72 will be turned on before a piston activated switch 74, giving a diagnosing physician information regarding the time required by the subject to exhale this first portion of breath. This is illustrated in FIG. 4 by the straight portion 86 of its graph 88 for nearly the first fraction second. The recording card 38 is calibrated so that the starting position 92 for the pen 42 corresponds to 200 ml. of expired breath.

As can be seen from FIG. 4, the final portion 91 of a subject's breath is exhaled much more slowly than the first portion. Since an air activated switch is sensitive to flow, it will be prone to open during this last portion of the breath.

Since neither of these two arrangements of switches alone give optimum performance, it is desirable to use them in combination. The two switches are connected in parallel to achieve a logical "or" function. The two switch arrangements used in this device are described below.

The piston motion activated switch 74 is held open by means of a tab 93 attached to the card holder 34. When the piston 14 moves from its initial position, tab 93 lifts away from switch 74 and allows it to close. Switch 72 is a normally open switch activated when air is displaced from the upper chamber 24 as detailed in FIGS. 3a and 3b.

Figure 3A:
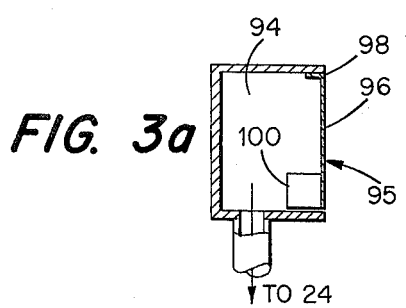
FIGS. 3a and 3b are cross-sectional views which detail an element of the embodiment of FIG. 1.
Figure 3B:
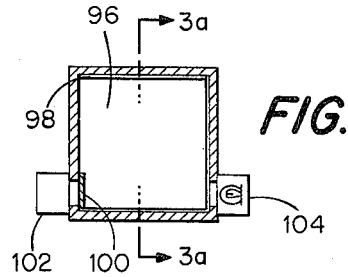

Referring to FIGS. 3a and 3b, air from the upper chamber 24 enters the chamber 94 having an opening to the atmosphere 95 which is covered by a thin vane 96. The vane may be constructed of a suitable material such as paper, foil, metal or plastic. The vane 96 is attached to the chamber by means of a hinge 98. Air entering the chamber blows the vane outward. The tab 100 on the vane is interposed between a light-sensitive device 102 and a light source 104, so that when the vane 100 moves light impinges upon the photo-sensitive device. When this occurs, the switch means turns on. Although the switch means of the preferred embodiment is a triac 106, a photosensitive device controlling a mechanical relay could be used. When the switch means used is a triac 106, it may be conveniently triggered by placing a photo resistor 102 between one of the ac terminals of its traic and the gate 108. Since the photo resistor conducts only when exposed to light, trigger current from the ac terminal flows to the gate 108 through the photo resistor 102 when the vane 100 is displaced by moving air.

Before commencing another test, using either the same card or another, the testing physician must cause the spirometer to return to its initial condition. He does this by opening the switch 70 and closing return mode activate switch 76. The normally closed limiting switch 78 opens when the pen holder 44 contacts it, interrupting current to the motor 52 and causing it to stop rotation. The mechanical arrangement described hereinbefore allows the pen holder to return to its starting position without marking the card, and the switching arrangement allows accurate repetition of starting positions. This allows the testing physician to obtain two or more superimposed traces on the same card which may be visually evaluated easily.

In order to avoid application of power through both the return and mark mode circuits simultaneously, it is possible to arrange to mark mode enable switch 70 and the return mode activate switch 76 so that they cannot be closed simultaneously. This is conveniently done by operating both switches by a rocker device (not shown), which may take the form of a two-way rocker switch with a center "off" position.

The simplicity of the design of the invention makes it compact and reliable. The use of a single piece molded seal allows for construction of a device of square or rectangular shape, further adding to the compactness.

While the invention is described with respect to the details of various specific embodiments, many changes and variations which can be made without departing from the scope of the invention will be apparent to those skilled in the art.

I claim:

1. A recording spirometer comprising:
   chamber means;
   piston means in said chamber means;
   a pair of rigid, substantially vertical posts mounted on one side of said piston means and situated adjacent opposite portions of said piston means;
   guide means for said piston means mating with said posts for allowing rectilinear motion of said posts along said guide means;
   means forming an air tight seal between said piston means and said chamber means; said chamber means, piston means, posts, guide means and seal means together forming a substantially air tight expansible chamber on a second side of said piston means opposite said one side;
   means forming an opening through which expiratory flow is introduced into said expansible chamber, the introduction of expiratory flow producing movement of said piston means;
   means mounted on the one side of said piston means for holding a recording surface, such recording surface when so held being movable rectilinearly with said piston means;
   means for marking such recording surface; and
   means for moving said marking means in substantially a straight line across such recording surface at a rate which is a known function of time, whereby simultaneous movement of said piston means and said marking means produces a plot of expiratory flow as a function of time.

2. The spirometer of claim 1 wherein said seal means comprises
a one-piece molded flexible rolling seal interposed between said piston means and said chamber means.

3. The spirometer of claim 2, wherein said chamber means comprises two mating sections and said one piece flexible seal is interposed between said mating sections to form an air-tight seal therebetween.

4. The spirometer of claim 3, wherein at least one of said mating sections comprises a peripheral groove along the mating edge thereof and said one piece flexible seal comprises a lip engaging said groove.

5. The spirometer of claim 1, wherein said holding means holds a substantially flat recording surface.

6. The spirometer of claim 5, wherein said holding means comprises
a substantially flat rigid plate mounted substantially vertically between said pair of vertical posts.

7. The spirometer of claim 1, wherein said guide means comprises rigid lubricating thermoplastic material in contact with said posts.

8. The spirometer of claim 1, wherein:
said piston means comprises a substantially rectangular plate with turned up edges; and
said vertical posts are mounted substantially perpendicular to the plane of said piston means so that the center of pressure of said piston means is substantially equidistantly spaced between said posts.

9. The spirometer of claim 1, further comprising:
light source means;
a photo sensitive device positioned to receive light from said light source means;
vane means movable to a first position for blocking the path between said light source means and said photo sensitive device and to a second position for unblocking said light path;
means supporting said vane means for movement between said first and second position in response to expiratory flow; and
electrical means for activating said means for moving said marking means in response to the amount of light impinging on said photo sensitive device.

10. The spirometer of claim 9 further comprising:
switch means operated by the motion of said piston means; and
second electrical means for activating said means for moving said marking means when said switch means is operated by said piston means, wherein said second electrical means and the first said electrical means are electrically connected to activate said marking means as a logical "or" function.

11. The spirometer of claim 10, wherein said switch means comprises:
a switch and means on said holding means for holding said switch open when said piston means is in an initial position, said switch otherwise being closed.

12. Control means for a recording spirometer, said spirometer including a chamber expansible as a function of expiratory flow and recording means, said control means comprising:
first switch means for initiating operation of said recording means in response to expansion of said chamber;
second switch means for initiating operation of said recording means in response to passage of expiratory flow to said chamber; and
means electrically connecting said first and second switch means for permitting either of said switch means, acting individually, to initiate operation of said recording means.

13. The device of claim 12, wherein said second switch means comprises:
a movable vane;
a light source;
photo-sensitive switch means;
means forming a light path between said light source and said photo-sensitive switch means which is unmasked in a first position of said vane but which is masked in a second position of said vane;
means supporting said vane for movement between two such positions in response to expiratory flow for varying light incident on said photo-sensitive switch means; and
means for initiating operation of said recording means in response to the amount of light impinging on said photo-sensitive switch means.

14. The device of claim 13, wherein said photo-sensitive switch means comprises:
a triac;
a photo-resistor;
an electrical connection between the gate of said triac and a first terminal of said photo-resistor; and
means providing a source of electrical energy connected to the second terminal of said photo-resistor sufficient to trigger said triac when said photo-resistor is exposed to light from said light source, but insufficient to trigger said triac when said photo-resistor is not exposed to said light.

15. The device of claim 14, wherein said photo-resistor is connected directly between said gate of said triac and one other terminal of said triac.

16. A recording spirometer comprising:
means for mounting a recording surface;
means for moving said mounting means as a function of air exhaled by a subject;
a threaded shaft rotatably mounted adjacent the path of movement of said mounting means;
marking means mounted on said shaft for rotary movement about the longitudinal axis thereof and engaging the threads thereof with sufficient friction to cause said marking means in its unrestrained condition to rotate with said shaft, said marking means being positioned to intercept such recording surface upon rotation thereof in one direction;
stop means to intercept said marking means upon rotation thereof in the opposite direction; and
reversible motor means for rotating said shaft in a first direction thereby to bring said marking means into contact with such recording surface and thereafter causing said marking means to traverse said shaft and for rotating said shaft in a second opposite direction thereby to bring said marking means into contact with said stop means and thereafter causing said marking means to traverse said shaft in the reverse direction.

17. The spirometer of claim 16 further comprising means for rotating said shaft at substantially constant angular velocity.

18. A recording spirometer comprising:
means forming an expansible chamber for receiving expiratory flow;

means forming an air filled chamber having a movable wall means in common with said expansible chamber for displacing air from said air filled chamber upon expansion of said expansible chamber;

electrically actuated recording means; and switch means responsive to flow of air from said air filled chamber for activating said recording means.

19. The spirometer of claim 18, wherein said switch means comprises:

vane means movable in response to flow of air from said air filled chamber; and second switch means for activating said recording means responsive to motion of said vane means.

20. The spirometer of claim 19, wherein said second switch means comprises:

a light source;

a photo-sensitive device;

means for activating said recording means in response to light impinging on said photo-sensitive device; and means forming an interruptable light path between said light source and said photo-sensitive device, said vane means being mounted for modulating the amount of light impinging upon said photo-sensitive device as a function of position of said vane means.

* * * * *